United States Patent
Danaboyina et al.

(10) Patent No.: US 6,770,787 B2
(45) Date of Patent: Aug. 3, 2004

(54) HEAVIER HALOGEN ATOM SUBSTITUTED SQUARAINE BASED DYES, PROCESS FOR THE PREPARATION THEREOF AND USE THEREOF AS SENSITIZERS FOR PHOTODYNAMIC, THERAPEUTICAL AND INDUSTRIAL APPLICATIONS

(76) Inventors: Ramaiah Danaboyina, Regional Research Laboratory (CSIR), Thiruvananthapuram, Kerala (IN), 695 019; Arun Kalliat Thazhathveetil, Regional Research Laboratory (CSIR), Thiruvananthapuram, Kerala (IN), 695 019; Suresh Das, Regional Research Laboratory (CSIR), Thiruvananthapuram, Kerala (IN), 695 019; Bernd Epe, Institut fur Pharmazie, Universitat Mainz, Mainz (DE), D-55099

( * ) Notice: Subject to any disclaimer, the term of this patent is extended or adjusted under 35 U.S.C. 154(b) by 460 days.

(21) Appl. No.: 09/753,751

(22) Filed: Jan. 2, 2001

(65) Prior Publication Data

US 2002/0123532 A1 Sep. 5, 2002

(51) Int. Cl.[7] .............................................. C07L 45/00
(52) U.S. Cl. ........................ 568/315; 568/317; 514/699
(58) Field of Search .................................. 568/315, 317

(56) References Cited

FOREIGN PATENT DOCUMENTS

WO          WO00/44742          7/1998        ......... C07D/335/06

OTHER PUBLICATIONS

Halogenated Squaraine Dyes as Potential Photochemotherapeutic Agents. Synthesis and Study of Photophysical Properties and Quantum Efficiencies of Singlet Oxygen Generation. Photochemistry and Photobiology (1997) 65(5): 783–790.

*Primary Examiner*—Paul J. Killos
(74) *Attorney, Agent, or Firm*—Darby & Darby

(57) ABSTRACT

The present invention relates to heavier halogen atom substituted squaraine based dyes of the formula 1 below

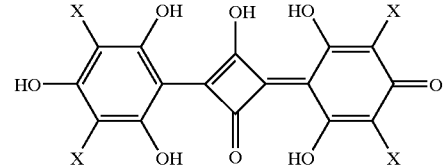

Figure 1:
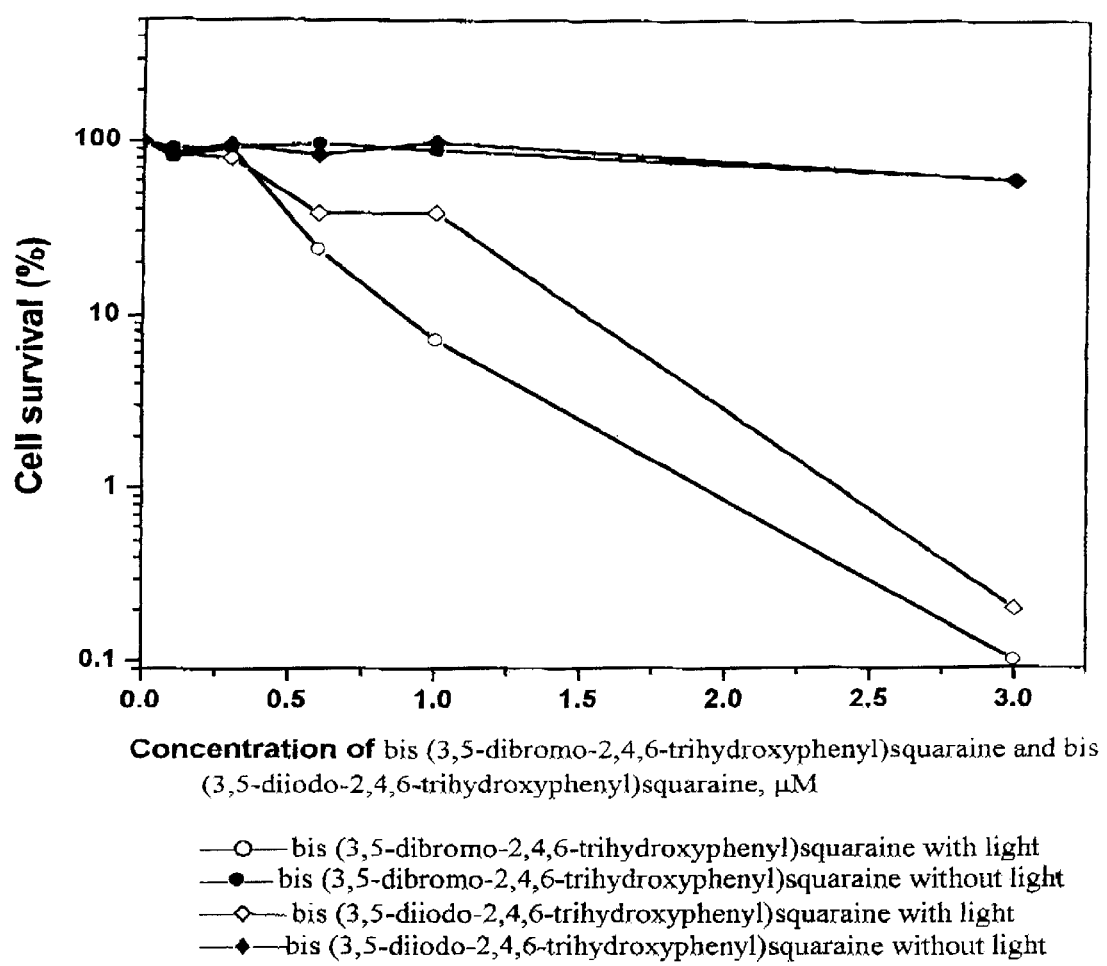

FIG. 1 where X is a heavier halogen atom and pharmaceutically acceptable derivatives thereof, which can be used in photodynamic therapeutical and industrial applications, and to a process for the preparation thereof.

7 Claims, 5 Drawing Sheets

O bis (3,5-dibromo-2,4,6-trihydroxyphenyl)squaraine with light
● bis (3,5-dibromo-2,4,6-trihydroxyphenyl)squaraine without light

HEAVIER HALOGEN ATOM SUBSTITUTED SQUARAINE BASED DYES, PROCESS FOR THE PREPARATION THEREOF AND USE THEREOF AS SENSITIZERS FOR PHOTODYNAMIC, THERAPEUTICAL AND INDUSTRIAL APPLICATIONS

FIELD OF THE INVENTION

The present invention relates to heavier halogen atom substituted squaraine based dyes of the formula 1 below

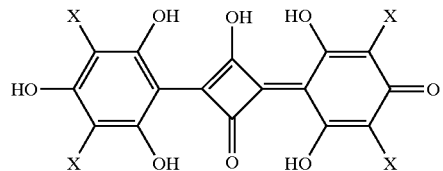

FIG. 1 wherein X is a heavier halogen atom and pharmaceutically acceptable derivatives thereof, which can be used in photodynamic therapeutical and industrial applications. The present invention also relates to a process for the preparation of heavier halogen atom substituted squaraine based dyes and use of such dyes as sensitizers for photodynamic, therapeutical and industrial applications.

The present invention also relates to squaraine dyes of formula 1 wherein X is bromine or ioidine or pharmaceutically acceptable derivatives thereof, which can be used as photosensitizers in photodynamic applications for diagnosis and treatment of cancer and other diseases in human beings or animals.

The present invention also relates to squaraine dyes of formula 1 wherein X is a heavy halogen atom or derivatives thereof, which can be used as photosensitizers in photodynamic industrial applications for sterilization of water.

BACKGROUND OF THE INVENTION

Photodynamic therapy is a latest modality for the diagnosis and treatment of cancer and various diseases. The large body of the evidence suggests that photodynamic therapy represents a convenient and effective approach for a variety of cancers. Photodynamic therapy involves the inactivation of living cells by the combined action of light and a chemical (photosensitizer). After intravenous injection, the photosensitizer is selectively retained by the tumor cells. There is more sensitizer in the tumor tissue than in the normal tissues. When irradiated with a light of specific wavelength or laser, the sensitizer produces highly reactive species. These highly reactive species alter the biological tissue and cause the selective destruction of the cancer cells.

The only sensitizer that has been extensively studied is Photofrin (porfime sodium), a hematoporphyrin derivative (HpD), also known as first generation photosensitizer. Photofrin and its commercial variants Photosan, Photogen were the first ones to be approved in clinical use and for which first regulatory authorizations were obtained. However, Photofrin is at the disadvantage of being a mixture of products the composition of which is highly sensitive to the synthetic methodology adopted. It is known to cause cutaneous photosensitivity as an undesirable side effect because of its slow release from the body. Under these circumstances, a patient treated with Photofrin is required to stay in the dark for a long period until it is excreted from the body. Photofrin possess only weak absorption in the red region of spectrum (the molar absorption coefficient being as small as 3000 $M^{-1}cm^{-1}$ at 630 nm), leading to difficulty in delivering light to some tumor sites and also incomplete light penetration of larger tumors. Therefore, photodynamic therapy using Photofrin is only indicated for cancers developing in the surface layers of less than 10 mm depth. References may be made to Dougherty, T. J. *Photochem. Photobiol.* 1987, 45, 879; Kessel, D.; Dougherty, T. J. *Phorphyrin Photosensitization;* Plenum Publishing Corp. New York, 1983; Brown, S. B.; Truscott, T. G. *Chem. Ber,* 1993, 29, 955; Andreoni, A., Cubeddu, R. *Phorphyrins in Tumor Phototherapy;* Plenum Publishing Corp.: New York, 1984; Brasseur, N.; Hasarat, A., Langlois, R., Wagner, J. R; Roussean, J.; van Lier J. E. *Photochem. Photobiol.* 1987, 45, 581; Spikes, J. D, *Photochem. Photobiol.* 1986, 43, 691; Firey, P. A.; Ford, W. E.; Sounik, J. R.; Kenney, M. E.; Rodgers, M. A. J. *J. Am. Chem. Soc.* 1988, 110, 7626; Moan, J. *Cancer Lett.* 1986, 33, 45; Tralau, C J., Young, A. R.; Walker, N. P. J.; Vernon, D. I.; MacRobert, A. J., Brown, S. B.; Brown, S. G. *Photochem. Photobiol.* 1989, 49, 305.

To overcome the drawbacks of the first generation sensitizers, second generation photosensitizers that exhibit strong absorptions in the long wavelength region have been synthesized. Second generation sensitizers that are under evaluation at various clinical phases of photodynamic therapy include chlorins, porphycenes, benzoporphyrins, phthalocyanins, purpurins and aminolevulinic acid-mediated porphyrins. Purpurins possess favorable optical properties and biodistribution patterns but require solubilizing or emulsifying agents such as liposomes or lipoproteins for their photodynamic applications. Chlorins have strong absorption in the red and infrared regions of the spectrum and compete favorably with Photofrin, but skin photosensitivity is a major problem with them. Phthalocyanins and metallophthalocyanins have been found to have strong absorption in the 600–700 nm region, but details of the extent of sulfonation versus the photodynamic activity is not clear. References may be made to U.S. Pat. Nos. 603,267; 5,965,598; 5,889,181; 586,035; 5,789,586; Kostenich, G. A.; Zuravkin, I. N.; Zhavrid, E. A. *J Photochem. Photobiol. B. Biol.* 1994, 22, 211; Leach, M. W.; Higgins, R. J.; Autry, S. A.; Boggan, J. E.; Lee, S. -J. H.; Smith, K. M. *Photochem. Photobiol.,* Bai, S.; Liu, C.; Guo, Z. *Proc. SPIE* 1993, 1616, 275; Vogel, E.; Kocher, M Schmickler, H.; Lex, J. *Angew. Chem. Int. Ed. Engl.* 1986, 25, 197; Leunig, M,; Richert, C.; Gamarra, F.; Lumper, W.; Vogel, E.; Jochani D.; Goetz, A. E. *Br. J. Cancer* 1993, 68, 225; Boyle, R. W.; Legnoff, C. C.; Vanheir, J. E. *Br. J. Cancer,* 1993, 67, 1177; Wohrl, D.; Shopova, M.; Muller, S.; Muleiv, A. D.; Mantereva, V. N.; Krastev, K. K. *J Photochem. Photobiol. B. Biol.* 1993, 21, 155; Morgan, A. R.; Garbo, G. M.; Keck, R. W.; Ericksen, L. D.; Selman, S. H. *Photochem. Photobiol.* 1990, 51, 589.

Development of photosensitizers, which have strong absorptions in the long wavelength region, non-toxic to normal tissues, soluble in buffer at physiological pH, can be bleached during the photodynamic treatment and exhibit higher therapeutic efficacy are still desired.

Squaraines form a class of dyes possessing sharp and intense absorption bands in the red to near infra red region. The molar absorption coefficients of these dyes are normally in the range of 500,000 $M^{-1}cm^{-1}$. Squaraines find industrial applications in xerographic photoreceptors, solar cells and optical recording devices. However, due to the very low intersystem crossing efficiency of these dyes, their potential as photosensitizers in photodynamic therapeutical applications have not yet been explored. References may be made to U.S. Pat. Nos. 6,001,523; 5,552,253; 5,444,463; Law, K.-Y. *Chem. Rev.* 1993, 93, 449; Piechowski, A P; Bird, G. R.; Morel, D L.; Stogryn, E. L. *J. Phy. Chem.* 1984, 88, 934.

Accordingly, the use of squaraine based dyes was studied to observe if the problems associated with the prior art could be overcome. It is an objective of this invention to provide a photosensitizer suitable for photodynamic therapeutical applications based on the squaraine moiety. Preliminary investigations by us indicated that halogenation of the squaraine moiety resulted in increased water solubility and intersystem crossing efficiency when compared to the parent unsubstituted squaraine dye. These halogenated dyes exhibited strong absorptions in the near infrared region (>600 nm) and significant bathochromic shifts in presence of microheterogeneous media. Triplet excited states were the main transients involved in these systems, which interact efficiently with molecular oxygen generating biologically highly reactive singlet oxygen in quantitative yields thereby making them potential candidates in phototherapeutical applications. Reference may be made to Ramaiah, D.; Joy, A.; Chandrasekhar, N; Eldho, N. V.; Das, S.; George, M. V. *Photochem. Photobiol.* 1997, 65, 783.

However, the yields of these halogenated squaraine dyes were of lower order under stipulated conditions and their efficiency of singlet oxygen (cytotoxic agent) generation in membrane modeling and drug carrier systems like polymers is not known. Moreover, there are no reports on biological properties or the photodynamic therapeutical applications of squaraine based dyes in the literature. The biological properties that are important to determine the use of sensitizers in photodynamic therapeutical applications include the sensitizer's stability under physiological pH and irradiation conditions, cellular toxicity, pharmacological aspects, genotoxicity and efficiency of its in vivo photodynamic activity etc.

The present invention is an attempt to overcome the above mentioned limits. By modified process conditions in the present invention, we have obtained enhanced yields of squaraine based dyes modified with heavier halogen atoms. We have investigated for the first time the biological properties of representative squaraine based photosensitizers. These investigations include the stability of these sensitizers under physiological pH conditions, cytotoxicity and mutagenicity in the dark and under irradiation conditions. Further in vivo and in vitro efficiency and mechanism of photodynamic activity of these sensitizers was investigated.

OBJECTS OF THE INVENTION

The main object of the present invention is to provide efficient squaraine based dyes and or pharmaceutical acceptable derivatives thereof, which can be used as sensitizers in photodynamic therapeutical applications including the treatment of cancer.

Another object of the present invention is to provide squaraine based dyes and/or or pharmaceutical derivatives thereof that can be used as fluorescent sensors for the diagnosis of cancer due to their significant fluorescent quantum yields in microheterogeneous media.

Yet another object of the present invention is to provide squaraine based dyes and/or their derivatives that can be used for photodynamic industrial applications such as sterilization of water etc.

Still another object of the present invention is that squaraine based dyes by linking them or introducing them in chemical devices, biological specificity to deliver or target such drug to defined kind of living cells can be achieved thereby efficient third generation photosensitizers can also be developed.

BRIEF DESCRIPTION OF THE ACCOMPANYING DRAWINGS

In the drawings accompanying the specifications

Figure 2:
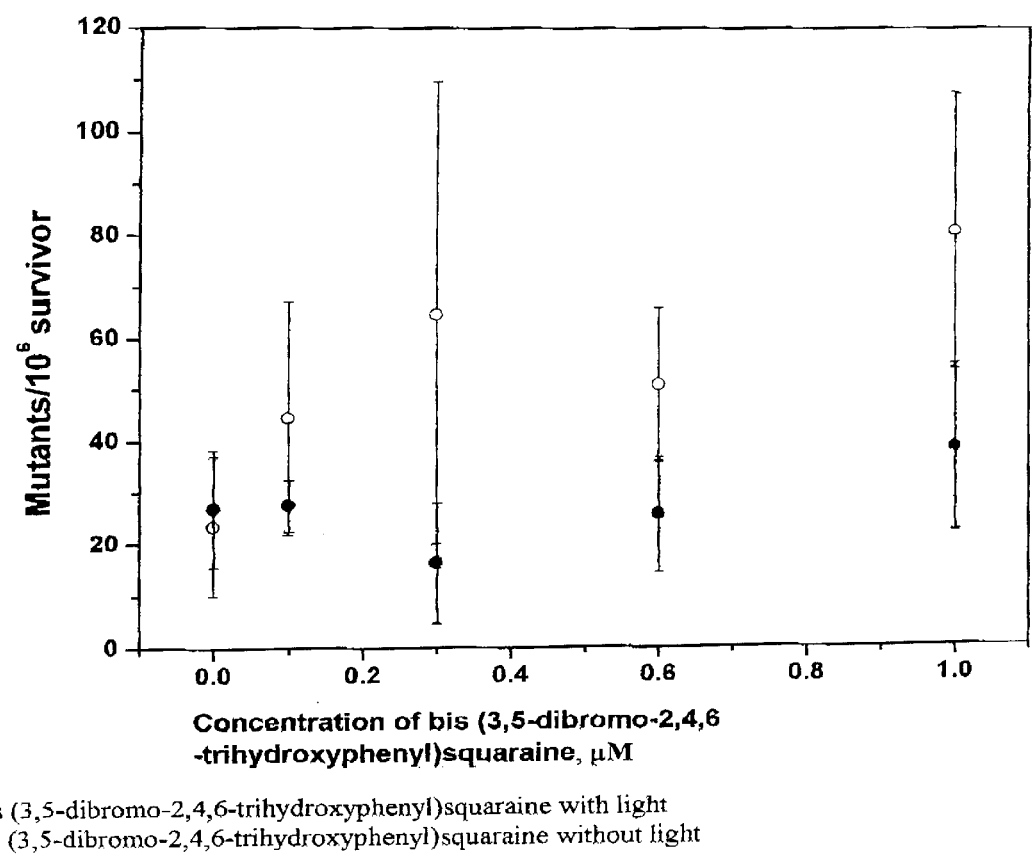
Figure 3:
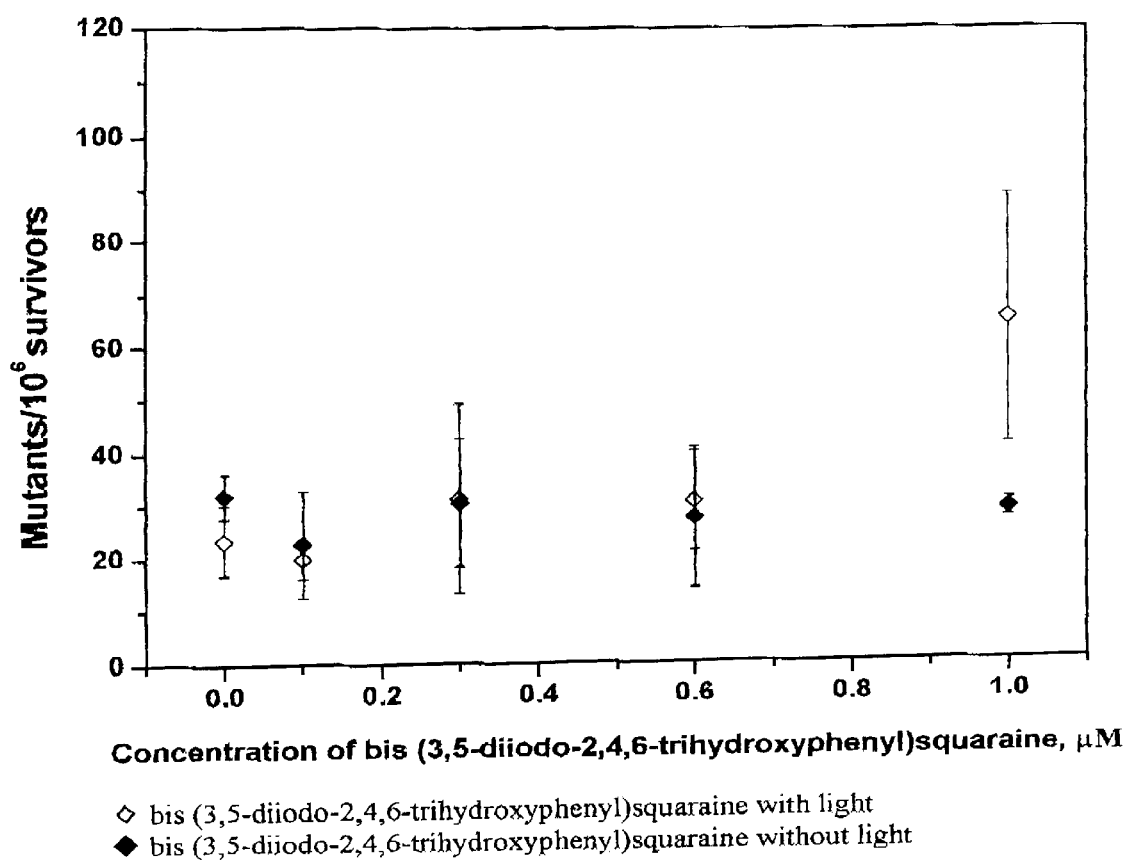
Figure 4:
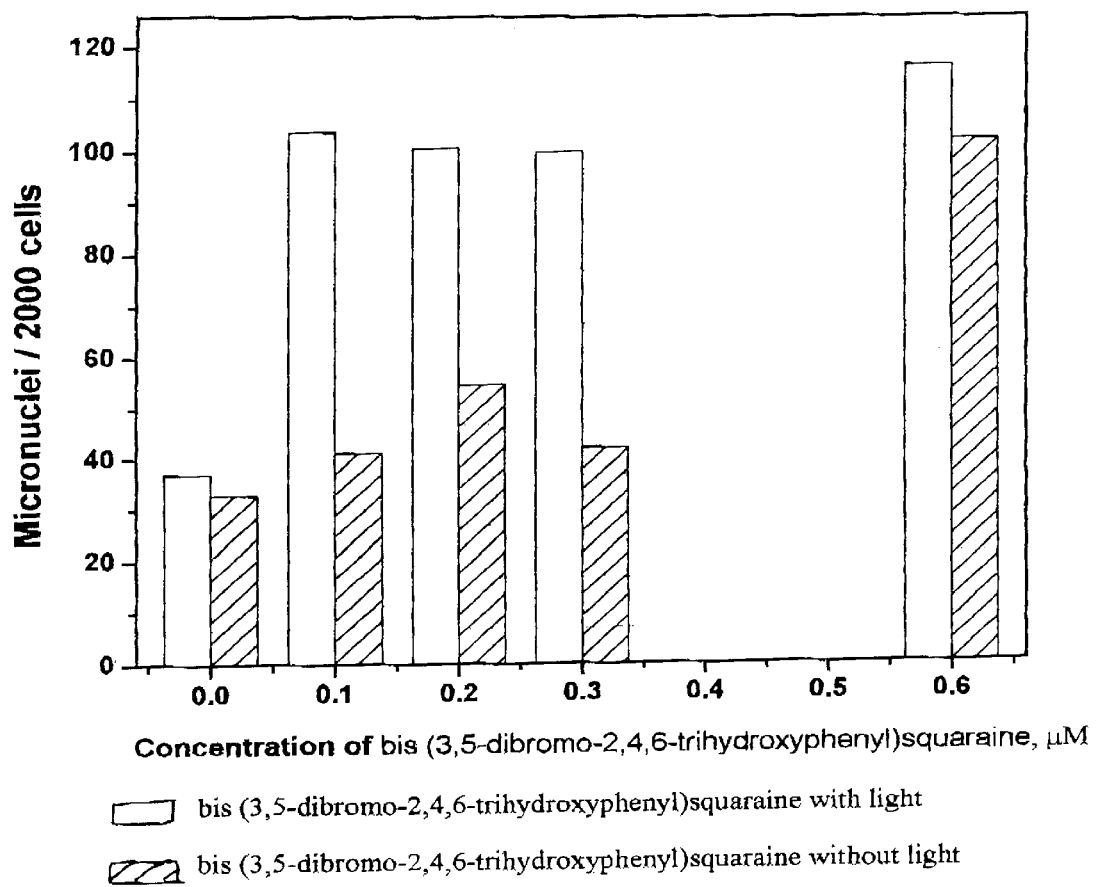
Figure 5:
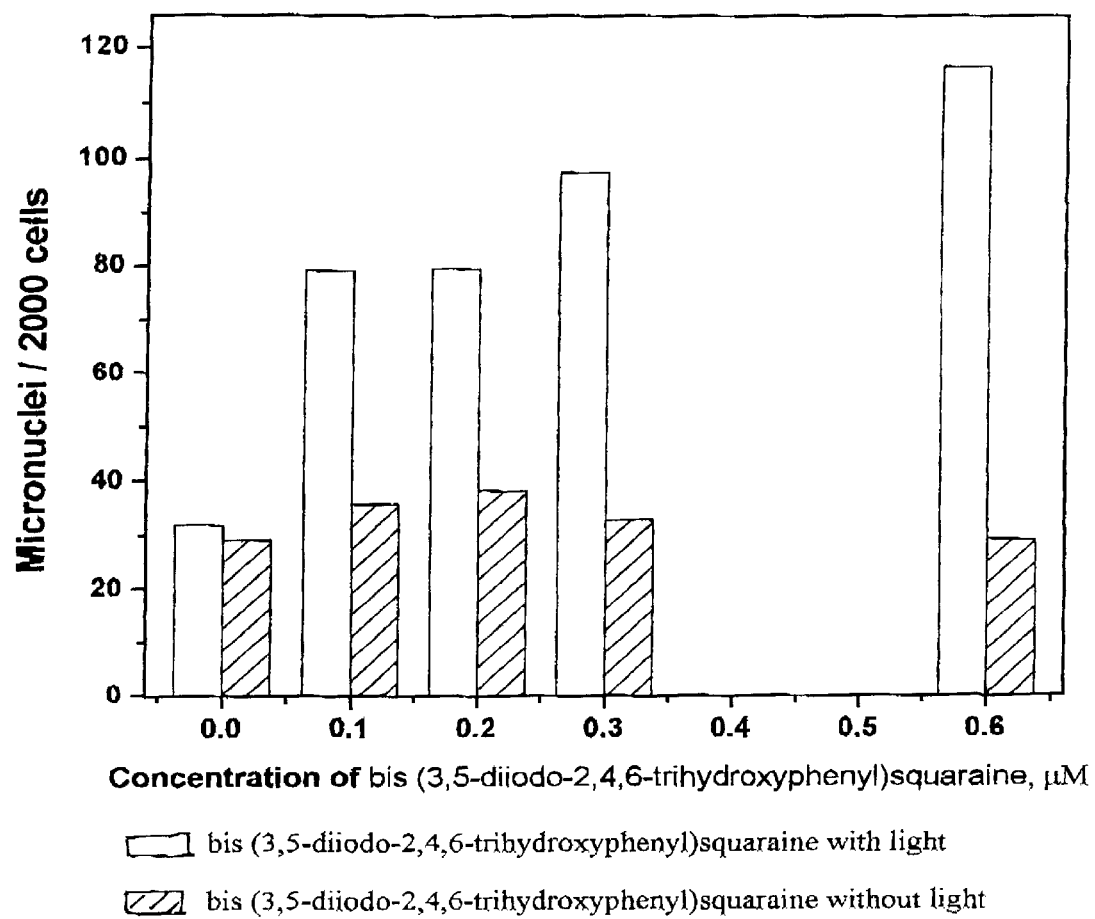

FIG. 1 represents the graph showing the cell killing efficiency of squaraine dyes of formula 1 in presence and absence of light FIG. 2 represents the graph showing the induction of mutants by bis(3,5-dibromo-2,4,6-trihydroxyphenyl) squaraine in presence and absence of light FIG. 3 represents the graph showing the induction of mutants by bis(3,5-diiodo-2,4,6-trihydroxyphenyl)squaraine in presence and absence of light FIG. 4 represents the graph showing the induction of micronuclei by bis(3,5-dibromo-2,4,6-trihydroxyphenyl) squaraine in presence and absence of light FIG. 5 represents the graph showing the induction of micronuclei by bis(3,5-diiodo-2,4,6-trihydroxyphenyl) squaraine in presence and absence of light

SUMMARY OF THE INVENTION

Accordingly, the present invention relates to a heavier halogen atom substituted squaraine dye of the general formula 1, wherein X is a heavier halogen atom and pharmaceutically acceptable derivatives thereof.

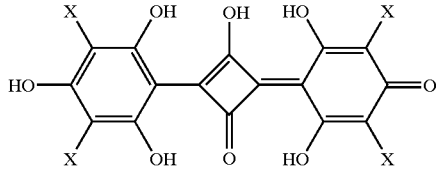

Formula 1

In one embodiment of the invention, X is selected from bromine or iodine.

In another embodiment of the invention, the compound of formula 1 is bis(3,5-dibromo-2,4,6-trihydroxyphenyl) squaraine.

In another embodiment of the invention, the compound of formula 1 is bis(3,5-diiodo-2,4,6-trihydroxyphenyl) squaraine.

The present invention also relates to a process for the preparation of heavier halogen atom substituted squaraine dye of the general formula 1 wherein X is a heavier halogen atom, or pharmaceutically acceptable derivatives thereof,

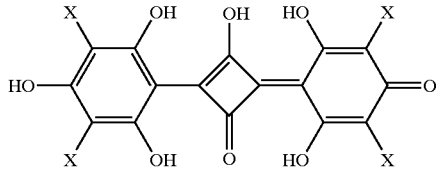

Formula 1 which comprises reacting bis (2,4,6, trihydroxyphenyl) squaraine with a halogen solution or a halogen salt in an organic acid under stirring at a temperature in the range of 50–80° C. for a time period ranging from 1–5 hours, cooling the above reaction mixture, filtering and washing the resultant compound followed by recrystallisation to obtain the desired compound.

In one embodiment of the invention, the halogen salt is a halogen monochloride.

In another embodiment of the invention, the organic acid is glacial acetic acid.

In a further embodiment of the invention, water is added to the reaction mixture before the steps of filtering and washing.

In yet another embodiment of the invention, the halogen atom is selected from bromine and iodine.

The invention also relates to the use of the compound of formula 1 as photosensitizers in photodynamic therapeutical applications.

In another embodiment of the invention, the compound of formula 1 is used as fluorescent detectors of tumours and in the photodynamic treatment of cancer and other related diseases.

The invention also relates to the use of the compound of formula 1 as a sensitizer in the sterilisation of water.

The invention also relates to the use of the compound of formula 1 in designing efficient third generation photosensitizers by introducing it into chemical devices to target such drugs to defined living cells.

DETAILED DESCRIPTION OF THE INVENTION

In the preparation of the compound of formula 1 the aromatic ring of bis(2,4,6-trihydroxyphenyl)squaraine is modified with heavier halogens such as bromine tyo obtain bis(3,5-dibromo-2,4,6-trihydroxyphenyl)squaraine and iodine to obtain bis(3,5-diiodo-2,4,6-trihydroxyphenyl) squaraine.

It is observed that compounds of structural formulae bis(3,5-dibromo-2,4,6-trihydroxyphenyl)squaraine and bis (3,5-diiodo-2,4,6-trihydroxyphenyl)squaraine having squaraine moiety and pharamaceutical derivatives thereof posses good solubility at physiological pH conditions and exhibit strong absorptions which extends well into the photodynamic window (>600 nm). These dyes are quite stable and non-toxic in the dark and exhibit good cell killing efficiency, when exposed to light. They undergo fast photobleaching and their photodegraded products are non-toxic in presence and absence of light. They do not induce significant mutations. Since the squaraine based dyes described above possess favourable photophysical and biological properties these compounds are highly suitable as photosensitizers for photodynamic therapeutical and industrial applications.

The following examples are given by way of illustration and therefore should not be construed to limit the scope of the present investigation.

EXAMPLE-1

Bis(2,4,6-trihydroxyphenyl)squaraine (Triebs, A.; Jacob, K. *Angew. Chem. Int. Ed. Engl.* 1965, 4, 694) was dissolved in glacial acetic acid (1:4.7×10³) by stirring the solution at 50–60° C. for 1–3 h. After cooling the solution bromine in acetic acid (1:1.7×10²) was added drop wise over a period of 1–2 h. The reaction mixture was heated at 50–60° C. for 1–2 h and was then kept in refrigerator for 10–12 h. The precipitate formed was filtered and washed with 75–100 mL of water. It was then recrystallized from a mixture of water and isopropanol (3:1) to give 75–85% of bis(3,5-dibromo-2,4,6-trihydroxyphenyl)squaraine.

The physiochemical properties of bis(3,5-dibromo-2,4,6-trihydroxyphenyl) squaraine: Melting point 314–315° C., IR (KBr) $v_{max}$ 3413, 1622, 726 and 519 cm$^{-1}$; Molecular Weight: Calculated 642.6874; Found 642.6879(HRMS); UV [20% v/v methanol-water] $\lambda_{max}$ 610 nm ($\epsilon$47000 M$^{-1}$cm$^{-1}$), [methanol] $\lambda_{max}$ 612 nm ($\epsilon$210000 M$^{-1}$cm$^{-1}$); Nature: Navy blue powder.

EXAMPLE-2

Bis(2,4,6-trihydroxyphenyl)squaraine (Triebs, A.; Jacob, K. *Angew. Chem. Int. Ed. Engl.* 1965, 4, 694) was dissolved in glacial acetic acid (1:4.7×10³) by stirring the solution at 60–70° C. for 1–2 h. After cooling, iodine monochloride in glacial acetic acid (1:1.7×10²) was added drop wise over a period of 1–2 h. The reaction mixture was heated at 50–60° C. for 1–2 h. 15 mL of water was added to the this and kept in the refrigerator for 10–12 h. The precipitate formed was filtered, washed with water (75–100 mL) and recrystallized from a mixture of methanol and isopropanol (3:1) to give 65–75% of bis(3,5-diiodo-2,4,6-trihydroxyphenyl) squaraine.

The physiochemical properties of bis (3,5-diiodo-2,4,6-trihydroxyphenyl) squaraine: Melting point 270–271° C.; IR (KBr)$v_{max}$ 3383, 1603, 726 and 568 cm$^{-1}$; Molecular Weight: Calculated 834.6320; Found 834.8360 (HRMS); UV [20% v/v methanol-water] $\lambda_{max}$ 617 nm ($\epsilon$63000 M$^{-1}$cm$^{-1}$), [methanol] $\lambda_{max}$ 620 nm ($\epsilon$249000 M$^{-}$cm$^{-1}$); Nature: Navy blue powder.

EXAMPLE-3

Because triplet excited states were the major transient intermediates obtained upon 532 nm laser flash photolysis studies of bis(3,5-dibromo-2,4,6-trihydroxyphenyl) squaraine and bis(3,5-diiodo-2,4,6-trihydroxyphenyl) squaraine, the efficiency of photosensitized singlet oxygen generation by these systems have been examined, since singlet oxygen is the main cytotoxic agent of the type II reactions in photodynamic therapy. Since singly deprotonated forms of bis(3,5-dibromo-2,4,6-trihydroxyphenyl) squaraine and bis(3,5-diiodo-2,4,6-trihydroxyphenyl) squaraine, have significant triplet yields and have long lifetimes (Ramaiah, D; Joy, A.; Chandrasekhar, N; Eldho, N. V.; Das, S.; George, M. V. *Photochem. Photobiol.* 1997, 65, 783), moreover these are the forms that are expected to be the predominant species under the biological pH conditions (around 7.4). The first level characterization of these dyes for using them as sensitizers in photodynamic therapy, we have investigated their efficiency of singlet oxygen generation in presence of drug carriers, membrane mimics and microheterogeneous media. Results obtained in presence of polyvinylpyrrolidone (PVP) using bis(3,5-dibromo-2,4,6-trihydroxyphenyl)squaraine and bis(3,5-diiodo-2,4,6-trihydroxyphenyl)squaraine are shown in TABLE 1.

TABLE 1 shows the efficiency of generation of singlet oxygen by bis(3,5-dibromo-2,4,6-trihydroxyphenyl) squaraine and bis(3,5-diiodo-2,4,6-trihydroxyphenyl) squaraine in presence and absence of polyvinylpyrrolidone

TABLE 1

| Compound | PVP, mM | singlet oxygen quantum yields |
|---|---|---|
| bis(3,5-dibromo-2,4,6-trihydroxyphenyl)squaraine | 0 | 0.13 ± 0.005 |
|  | 14 | 0.29 ± 0.001 |
| bis(3,5-diiodo-2,4,6-trihydroxyphenyl)squaraine | 0 | 0.47 ± 0.017 |
|  | 14 | 0.62 ± 0.007 |

The results show that there is significant increase in quantum yields of singlet oxygen generation in presence of PVP sensitized by both bis(3,5-dibromo-2,4,6-trihydroxyphenyl)squaraine and bis(3,5-diiodo-2,4,6-trihydroxyphenyl)squaraine. In the case of bis(3,5-diiodo-2,4,6-trihydroxyphenyl)squaraine, the efficiency of singlet oxygen generation is nearly 15% more in microheterogeneous media than in methanol. Furthermore, these studies indicate heavier halogen atoms substituted can act as efficient photosensitizers for photodynamic therapeutical applications.

EXAMPLE-4

The mechanism of in vitro photodynamic activity of squaraines has been evaluated in detail by using plasmid DNA (PM2 DNA) and investigating the cleavage of DNA under a variety of conditions. Cleavage of DNA cleavage was followed by monitoring the conversion of supercoiled (Form I) to open circular (Form II) and linear forms (Form III). Induction of one single strand break by a compound/agent converts Form I to Form II and the quantification of these forms by DNA relaxation assay as described previously (Epe, B.; Hegler, J. *J. Methods Enzymol.* 1994, 234, 122) indicates its efficiency of DNA cleavage. Plasmid DNA cleavage is a very sensitive technique, which can be used to test the various properties of sensitizers and the DNA damage profiles obtained by using scavengers and activators can serve as a kind of fingerprint of the species directly responsible for the damage and also provide the information on the mechanism of in vitro photodynamic activity.

PM2 DNA (10,000 bp, 10 µg/mL) exposed to squaraine dyes plus light from a 1000 W halogen lamp (Philips PF811) at a distance of 33 cm in phosphate buffer (5 mM $KH_2PO_4$, 50 mM NaCl, pH 7.4) on ice. The modified DNA was precipitated by ethanol/sodium acetate and quantified the single strand breaks (SSB) by DNA relaxation assay. Superoxide dismutase (SOD) (20 µg/ml), catalase (315 U/ml) were added or the $H_2O$ in the buffer was replaced by $D_2O$ (the final isotope purity was greater than 96%) to have a better understanding of the active species involved. The results of these studies with representative squaraine based dyes bis(3,5-dibromo-2,4,6-trihydroxyphenyl)squaraine and bis(3,5-diiodo-2,4,6-trihydroxyphenyl)squaraine are shown in TABLE 2.

TABLE 2 shows the efficiency of plasmid DNA cleavage by bis(3,5-dibromo-2,4,6 trihydroxyphenyl)squaraine and bis(3,5-diiodo-2,4,6-trihydroxyphenyl)squaraine in presence and absence of additives.

The results shown in TABLE 2 indicate that neither superoxide dismutase nor catalase has a significant effect on the efficiency of DNA cleavage induced by bis(3, 5-dibromo-2,4,6-trihydroxyphenyl)squaraine and bis(3,5-diiodo-2,4,6-trihydroxyphenyl)squaraine. Therefore, superoxide and hydrogen peroxide (a possible

TABLE 2

Relative number of single strand breaks (%) in presence of[a]

| Compound | pH 7.0 | PH 7.8 | $D_2O$ Buffer | SOD (20 g/mL) | Catalase (315 U/mL) |
|---|---|---|---|---|---|
| bis(3,5-dibromo-2,4,6-trihydroxyphenyl)-squaraine | 127 ± 12 | 105 ± 4 | 526 ± 28 | 109 ± 5 | 115 ± 5 |
| bis(3,5-diiodo-2,4,6-trihydroxyphenyl)-squaraine | 134 ± 9 | 109 ± 22 | 614 ± 97 | 100 ± 2 | 92 ± 6 |

TABLE 2-continued

Relative number of single strand breaks (%) in presence of[a]

| Compound | pH 7.0 | PH 7.8 | $D_2O$ Buffer | SOD (20 g/mL) | Catalase (315 U/mL) |
|---|---|---|---|---|---|

[a] number of single strand breaks (SSB) observed in phosphate buffer (pH 7.4) in the absence of an additive defined as 100%.

Subsequent Fenton reaction of these species are not involved in the cleavage of DNA. Nearly five and six fold enhancement in the cleavage of DNA induced by bis(3,5-dibromo-2,4,6-trihydroxyphenyl)squaraine and bis(3,5-diiodo-2,4,6-trihydroxyphenyl)squaraine in $D_2O$ is a strong indication that the in vitro photodynamic activity is mediated predominantly by singlet oxygen in these cases.

EXAMPLE-5

The information about the stability of the sensitizer in presence and absence of light is important for its practical use. Therefore, the stability of these dyes in presence and absence of light in ethanol and phosphate buffer at physiological pH conditions (pH 7.4) at 25° C. was studied by following the absorbance change using spectrophotometry. The results of change in absorbance vs time in the dark with representative squaraine based dyes bis(3,5-dibromo-2,4,6-trihydroxyphenyl)squaraine and bis(3,5-diiodo-2,4,6-trihydroxyphenyl)squaraine are shown in TABLE 3.

TABLE 3 shows the stability of bis(3,5-dibromo-2,4,6-trihydroxyphenyl)squaraine and bis(3,5-diiodo-2,4,6-trihydroxyphenyl)squaraine in ethanol and buffer (pH 7.4) in the dark

TABLE 3

| | Absorbance | | |
|---|---|---|---|
| Time in Dark, min | bis(3,5-dibromo-2,4,6-trihydroxyphenyl) squaraine (ethanol) | bis(3,5-dibromo-2,4,6-trihydroxyphenyl) squaraine (buffer) | bis(3,5-diiodo-2,4,6-trihydroxyphenyl) squaraine (buffer) |
| 0 | 1.90 | 1.84 | 1.35 |
| 30 | 1.88 | 1.72 | 1.47 |
| 60 | 1.88 | 1.65 | 1.38 |
| 90 | 1.88 | 1.61 | 1.36 |

Results in the dark show that the dyes bis(3,5-dibromo-2,4,6-trihydroxyphenyl)squaraine and bis(3,5-diiodo-2,4,6-trihydroxyphenyl)squaraine are very stable in ethanol but undergo slight bleaching in buffer solutions at pH 7.4 over a long period of 90 min. The results obtained with bis(3,5-dibromo-2,4,6-trihydroxyphenyl)squaraine and bis(3,5-diiodo-2,4,6-trihydroxyphenyl)squaraine in buffer at pH 7.4 under irradiation conditions are shown in TABLE 4.

TABLE 4 shows the stability of bis(3,5-dibromo-2,4,6-trihydroxyphenyl)squaraine and bis(3,5-diiodo-2,4,6-trihydroxyphenyl)squaraine in buffer (pH 7.4) under irradiation conditions

TABLE 4

| | Absorbance | |
|---|---|---|
| Irradiation time, min | bis(3,5-dibromo-2,4,6-trihydroxyphenyl)squaraine | Bis(3,5-diiodo-2,4,6-trihydroxyphenyl)squaraine |
| 0 | 1.8 | 1.72 |
| 5 | 1.35 | 0.87 |
| 10 | 1.30 | 0.74 |
| 15 | 1.25 | 0.65 |
| 20 | 1.17 | 0.58 |
| 30 | 1.10 | 0.47 |

Results under irradiation conditions (1000 W halogen lamp (Philips PF811) at a distance of 33 cm) show that these dyes exhibit significant photobleaching. Compound bis(3,5-diiodo-2,4,6-trihydroxyphenyl)squaraine undergoes very fast photobleaching (nearly 50% within 5 min of irradiation), when compared to bis(3,5-dibromo-2,4,6-trihydroxyphenyl)squaraine (25%). The photobleaching was increased with the time of irradiation in both the cases. While photobleaching might be thought to be disadvantageous property in a tumor photosensitizer, but it has potential benefits since dosage can be adjusted to keep the photosensitizer in tumor at effective levels. Moreover because of their fast photobleaching, a patient after the photodynamic treatment is not required to stay in the dark for long periods of time and if required therapy can be repeated frequently with short intervals of time.

EXAMPLE-6

To measure the cell killing efficiency (cytotoxicity) of squaraine based sensitizers with and without light, AS52 cells were exposed to various concentrations of sensitizer. The light exposure was carried out from a 1000 W halogen lamp at a distance of 33 cm in $Ca^{2+}$ and $Mg^{2+}$ free PBS (140 mM NaCl, 3 mM KCl, 8 mM $Na_2HPO_4$, pH 7.4) on ice ($10^6$ cells/ml). Illumination for 10 min corresponds to 225 $kJ/m^2$ between 400 and 800 nm. The cells were pelleted by centrifugation and resuspended in PBSG three times. The cells were resuspended at $3 \times 10^4$ cells/ml in fresh medium at 37° C. and the number of cells were counted repeatedly for 60 h. From the exponential part of the growth curves (between 24 and 60 h), the number of poliferating cells at the time of resuspension was calculated by extrapolation. Cell survival was defined as the ratio between proliferating and resuspended cells. Results obtained with representative squaraine based dyes bis(3,5-dibromo-2,4,6-trihydroxyphenyl)squaraine and bis(3,5-diiodo-2,4,6-trihydroxypheny)squaraine are shown in FIG. 1.

The results show that the % of cell survival decreases with the increasing in concentration of bis(3,5-dibromo-2,4,6-trihydroxyphenyl)squaraine and bis(3,5-diiodo-2,4,6-trihydroxyphenyl)squaraine under illumination conditions indicating their high cell killing efficiency under these conditions. At the same time bis(3,5-dibromo-2,4,6-trihydroxyphenyl)squaraine and bis(3,5-diiodo-2,4,6-trihydroxyphenyl)squaraine exhibit no significant effect in the dark indicating thereby their non-toxicity in the absence of light. These results clearly demonstrate the photodynamic therapeutical applications of heavier halogen atom substituted squaraine dyes.

EXAMPLE-7

The mutagenic properties of squaraine based sensitizers was measured in AS52 cells, which carry the bacterial guanine phosphoribosyltraiisferase (gpt) gene as a selection marker that confers sensitivity to 6-thioguanine. AS52 cells were cultured in cleansing medium containing 11 μg/ml xanthine 219 μg/ml xanthine, 22 μg/ml adenine, 1.2 μg/ml aminopterin and 8.8 μg/ml mycophenolic acid) for one week to eliminate spontaneous gpt mutants. Cells ($0.5 \times 10^6$) were incubated in recovery medium (containing 1.2 μg/ml thymidine, 11.5 μg/ml xanthine, 3 μg/ml adenine) for 48 h and then were exposed to bis(3,5-dibromo-2,4,6-trihydroxyphenyl)squaraine and bis(3,5-diiodo-2,4,6-trihydroxyphenyl)squaraine in presence and absence of light as described above and subsequently cultured for one week (expression time). During this time, exponential growth of cells was maintained. $2 \times 10^5$ cells were diluted in 10 ml culture medium and plated in petri dishes (94 mm) After 2 h, 6-thioguanine was added to each plate (final concentration 2.5 μg/ml) for selection. 200 cells were added in 5 ml culture medium and plated in petri dishes (60 mm) to determine the cloning efficiencies. The plates were incubated for 7 to 9 days. The medium was replaced by NaCl solution (0.9% v/v), the cell colonies were fixed with methanol (−20° C.) for 15 min and stained with Giemsa (10% in $H_2O$) for 15 min. The subsequent quantification of 6-thioguanine resistant cells and the determination of cytotoxicity (ratio of the plating efficiences of treated and untreated cells) directly after exposure to squaraines plus light carried out according to the protocol (Tindall, K. R.; Stankowski Jr. L. F.; Machanoff, R.; Hsie, A. W. *Mutat. Res.* 1986, 160, 121–131).

The results obtained are shown in FIG. 2 and FIG. 3, which indicate that bis(3,5-dibromo-2,4,6-trihydroxyphenyl)squaraine and bis(3,5-diiodo-2,4,6-trihydroxyphenyl)squaraine do not induce immediate mutations in presence and absence of light. Although severe cytotoxicity was observed in presence of light, no significant increase of the spontaneous mutation frequencies was observed, when compared to the dark and control values.

EXAMPLE-8

Further to understand the genetic effects, the micronuclei induced by bis(3,5-dibromo-2,4,6-trihydroxyphenyl) squaraine and bis(3,5-diiodo-2,4,6-trihydroxyphenyl) squaraine were also quantified in AS52 cells. AS52 cells were exposed to squaraines as described above and resuspended in full medium. After incubation for 24 h at 39° C., approximately $1 \times 10^5$ cells were fixed on a microscope slide by cytospin-centrifugation and treatment with methanol for 1 h at −21° C. After staining with bisbenzimide for 3 min in PBS (without $Ca_{2+}$ and $Mg_{2+}$), 2000 cells were examined for the presence of micronuclei with a fluorescent microscope. The results obtained are shown in FIG. 4 and FIG. 5, which indicate that these dyes do not induce significant amounts of micronuclei.

The squaraine based dyes of the present invention possess satisfactory properties of a photosensitizer for photodynamic therapeutical and industrial applications. The main advantages of these systems include:

1. Squaraine based sensitizers represented by structures bis(3,5-dibromo-2,4,6-trihydroxyphenyl)squaraine and bis(3,5-diiodo-2,4,6-trihydroxyphenyl)squaraine are pure single substances.
2. Their synthetic methodology is economical.
3. They are quite stable in the dark and their stability found to increase in presence of membrane models and carrier systems.
4. They have very good solubility in buffer at physiological pH conditions, therefore pharmaceutical preparation can be prepared by per se conventional procedures and avoids the use of additives and carriers.
5. They possess good absorption properties (>600 nm) with significant absorption coefficients (around 100,000 $M^{-1}cm^{-1}$).
6. They have good triplet yields with significant lifetimes and generate singlet oxygen in quantitative yields in membrane modeling and carrier systems.
7. They are non-toxic in the dark but show good cell killing when exposed to light, as expected of an ideal photosensitizer.
8. They undergo fast photobleaching therefore a patient after the photodynamic treatment is not required to stay in the dark for long periods of time and if required therapy can be repeated frequently with short intervals of time.
9. Their photodegraded byproducts are non-toxic in presence and absence of light.
10. Photodynamic activity of these dyes was maximum within 5 min exposure to light therefore requires very short irradiation time intervals for the treatment.
11. They are non-mutagenic.
12. They can be effectively used in the synthesis of $3^{rd}$ generation photosensitizers for targeting the defined cell organelles.

We claim:

1. A process for the preparation of heavier halogen atom substituted squaraine dye of the general formula 1 wherein X is a heavier halogen atom, or pharmaceutically acceptable derivatives thereof,

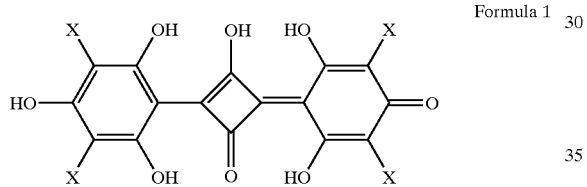

Formula 1 which comprises reacting bis(2,4,6, trihydroxyphenyl) squaraine with a halogen solution or a halogen salt in an organic acid under stirring at a temperature in the range of 50–80° C. for a time period ranging from 1–5 hours, cooling the above reaction mixture, filtering and washing the resultant compound followed by recrystallisation to obtain the desired compound.

2. A process as claimed in claim 1 wherein the halogen salt is a halogen monochloride.

3. A process as claimed in claim 1 wherein the organic acid is glacial acetic acid.

4. A process as claimed in claim 1 wherein water is added to the reaction mixture before the steps of filtering and washing.

5. A process as claimed in claim 1 wherein the halogen atom is selected from bromine and iodine.

6. A method of sterilizing water comprising adding a compound of formula 1 to water,

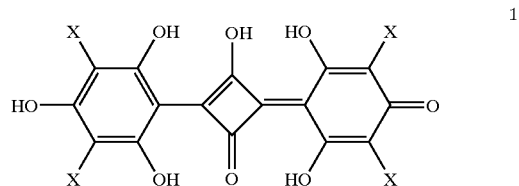

1 wherein X is a heavier halogen atom, and irradiating the compound to form a highly reactive species, which sterilizes the water.

7. A method of detecting tumors comprising:

exposing a tumor to a compound of formula 1,

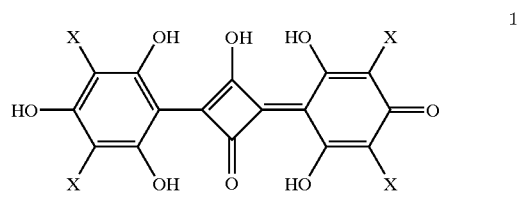

1 wherein X is a heavier halogen atom, wherein said compound is selectively retained by said tumor, irradiating said compound to make it fluoresce, detecting the fluorescence of said compound, and concluding that a tumor is present based on said fluorescence.

* * * * *